(12) United States Patent
Prince et al.

(10) Patent No.: US 6,491,819 B2
(45) Date of Patent: Dec. 10, 2002

(54) METHOD AND APPARATUS FOR FILTERING SUSPENSION OF MEDICAL AND BIOLOGICAL FLUIDS OR THE LIKE

(75) Inventors: Paul R. Prince, San Juan Capistrano, CA (US); Michael O. Pekkarinen, Lincolnshire, IL (US); David Bellamy, Jr., Kenilworth, IL (US); Shmuel Sternberg, Northbrook, IL (US)

(73) Assignee: Baxter International Inc., Deerfield, IL (US)

( * ) Notice: Subject to any disclaimer, the term of this patent is extended or adjusted under 35 U.S.C. 154(b) by 0 days.

(21) Appl. No.: 09/954,734

(22) Filed: Sep. 18, 2001

(65) Prior Publication Data

US 2002/0033367 A1 Mar. 21, 2002

Related U.S. Application Data

(62) Division of application No. 09/312,883, filed on May 17, 1999, which is a continuation of application No. 08/719,472, filed on Sep. 25, 1996, now abandoned.

(51) Int. Cl.$^7$ .............................................. B01D 61/14
(52) U.S. Cl. ............................ 210/321.67; 210/321.68; 210/321.87; 210/497.01
(58) Field of Search ....................... 210/321.38, 321.78, 210/321.87, 500.21, 500.22, 781, 497.01, 321.67

(56) References Cited

U.S. PATENT DOCUMENTS

| | | |
|---|---|---|
| 3,520,416 A | 7/1970 | Keedwell |
| 4,701,267 A | 10/1987 | Watanabe |
| 4,735,726 A | 4/1988 | Duggins |
| 4,797,175 A | 1/1989 | Ellion et al. |

(List continued on next page.)

FOREIGN PATENT DOCUMENTS

| | | |
|---|---|---|
| GB | 2 238 619 | 6/1991 |
| GB | 2 239 311 | 6/1991 |
| WO | WO 88/04184 | 6/1988 |
| WO | WO 91/11262 | 8/1991 |
| WO | WO 91/13338 | 9/1991 |
| WO | WO 93/23154 | 11/1993 |
| WO | WO 95/13860 | 5/1995 |
| WO | WO 97/12657 | 4/1997 |

OTHER PUBLICATIONS

1) International Search Report re WO Application No. PCT/US97/17071, mailed Dec. 22, 1997.
2) Handout accompanying presentation by Dr. Robert Austin entitled "Microlithographic Arrays," presented at the *Microfabrication technology for Research and Diagnostics* seminar held Sep. 28–29, 1995, San Francisco, California.

(List continued on next page.)

*Primary Examiner*—Joseph W. Drodge
(74) *Attorney, Agent, or Firm*—Andrew G. Kolomayets; Barry W. McFarron; Bradford R. L. Price

(57) ABSTRACT

An apparatus is disclosed for separating a suspension comprising at least two types of particles which are differently sized or shaped and in which the first type of particle may be deformable at a relatively lower force or faster rate than the second type of particle. A housing is provided having a generally cylindrical inner surface in which is mounted a rotor having a generally cylindrical outer surface. The outer surface of the rotor is spaced from the inner surface of the housing to define a suspension processing gap. A filter membrane is provided on the surface of the rotor or the housing that has pores with substantially precisely dimensioned shapes and sizes to correspond substantially to the shape of the first type of particle, thus allowing passage of the first type of particle and blocking passage of the second type of particle. A suspension is directed into the processing gap for either a selected residence time in contact with the filter membrane and/or at a selected force.

10 Claims, 7 Drawing Sheets

U.S. PATENT DOCUMENTS

| | | |
|---|---|---|
| 4,806,247 A | 2/1989 | Schoendorfer et al. |
| 4,808,307 A | 2/1989 | Fischel et al. |
| 4,871,462 A * | 10/1989 | Fischel et al. .......... 210/321.68 |
| 4,879,040 A | 11/1989 | Prince et al. |
| 4,923,608 A | 5/1990 | Flottmann et al. |
| 4,936,993 A | 6/1990 | Nomura |
| 4,994,188 A | 2/1991 | Prince |
| 5,034,135 A | 7/1991 | Fischel |
| 5,053,121 A * | 10/1991 | Schoendorfer et al....210/321.68 |
| 5,064,541 A | 11/1991 | Jeng et al. |
| 5,064,542 A | 11/1991 | Negersmith et al. |
| 5,069,792 A | 12/1991 | Prince et al. |
| 5,151,082 A | 9/1992 | Gorsuch et al. |
| 5,190,657 A | 3/1993 | Heagle et al. |
| 5,194,145 A | 3/1993 | Schoendorfer |
| 5,198,007 A | 3/1993 | Moyer et al. |
| 5,234,593 A | 8/1993 | Kuroki et al. |
| 5,234,594 A | 8/1993 | Tonucci et al. |
| 5,269,946 A | 12/1993 | Goldhaber et al. |
| 5,344,565 A | 9/1994 | Degen et al. |
| 5,376,263 A | 12/1994 | Fischel |
| 5,423,989 A | 6/1995 | Allen et al. |
| 5,427,663 A | 6/1995 | Austin et al. |
| 5,464,534 A | 11/1995 | Fischel |
| 5,543,046 A | 8/1996 | Van Rijn |
| 5,753,014 A | 5/1998 | Van Rijn |
| 5,807,406 A | 9/1998 | Brauker et al. |

OTHER PUBLICATIONS

3) Carlson, R.H. et al., "White Blood Cell Penetration and Fractionation in a Microlithographic Array," presented at the *Cambridge Healthtech Institute's 2$^{nd}$ Annual Microfabrication Technology for Biomedical Applications* seminar held Oct. 24–25, 1996 in San Jose, California.

4) Chien, S. et al., "Rheology of Leukocytes," *Annals New York Academy of Sciences*, pp. 333–347.

5) Chien, S. et al., "Viscoelastic Properties of Leukocytes," *White Cell Mechanics: Basic Science and Clinical Aspects*, pp. 19–51, 1984.

6) Nelson, T.E. et al., "Microfabrication of Porous Polyimide Membranes," The University of Illinois at Chicago Microfabrication Applications Laboratory, Department of Electrical Engineering & Computer Science, (submitted to the *183$^{rd}$ Meeting of the Electrochemical Society*, Inc. held May 16–21, 1993 in Hawaii).

7) Nelson, T.E. et al., "Fabrication of Microporous Polyimide Membranes", The University of Illinois at Chicago Microfabrication Applications Laboratory, Department of Electrical Engineering & Computer Science, (submitted to the *15$^{th}$ Annual International Conference of IEEE Engineering in Medicine and Biology Society*, held Oct. 28–31, 1993 in San Diego, California).

8) Reinhart, W.H. et al., "Evaluation of Red Blood Cell Filterability Test: Influences of Pore Size, Hematocrit Level and Flow Rate", *J. Clin. Med.*, vol. 101, No. 4, pp. 501–516, Oct., 1984.

9) Schmid–Schonbein et al., "Morphometry of Human Leukocytes," Blood, vol.56, No. 5, 1980.

\* cited by examiner

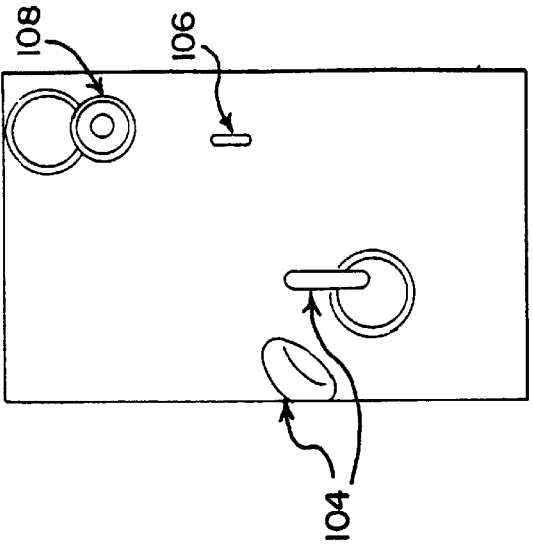
FIG.12a  3.0 μm PORES
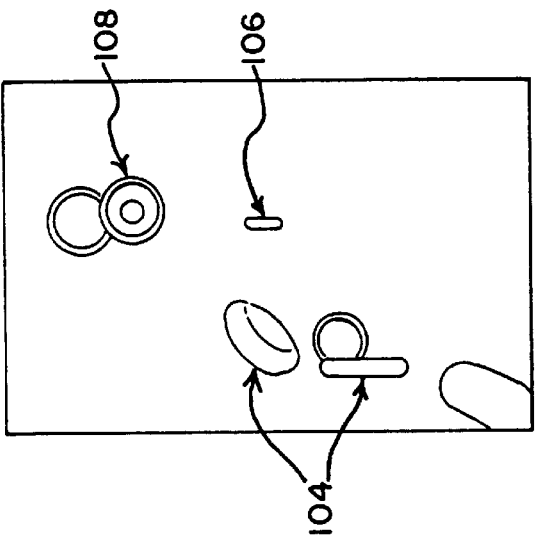
FIG.12b  4.0 μm PORES
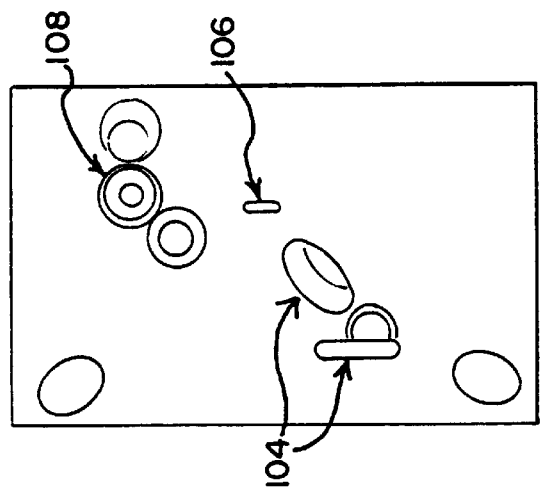
FIG.12c  5.0 μm PORES

METHOD AND APPARATUS FOR FILTERING SUSPENSION OF MEDICAL AND BIOLOGICAL FLUIDS OR THE LIKE

This application is a division of application Ser. No. 09/312,883, filed May 17, 1999, which is a continuation of application Ser. No. 08/719,472, filed Sep. 25, 1996, now abandoned.

The present invention relates generally to the separation of particles suspended in solution based upon unique characteristics of the various particles such as the shape, size and/or deformability, and more particularly to the selective separation or filtration of cells, cell components or fragments thereof which have one or more various unique physical characteristics.

BACKGROUND OF THE INVENTION

Techniques for the separation of constituents of various medical/biological fluids, such as whole blood, are in wide use for many diagnostic, therapeutic, and other medically-related, applications. For example, centrifugal separation based upon the different densities and settling velocities of the constituent components to be separated is well known. The CS-3000 separator, sold by Baxter Healthcare Corporation of Deerfield, Ill., is one example of a centrifugal separator that has been very successfully used in separating whole blood into constituent components, such as red blood cells (RBC), white blood cells (WBC), platelets, and plasma for collection or depletion of the desired components from a donor or patient. While centrifugation has proven to be a generally satisfactory method of achieving separation, in certain applications the purity of the separated components is not as high as desired due to the very close and/or overlapping densities and settling velocities of the different suspended particles.

Mesh and aggregate structures and membranes are also used to remove particles from suspension. Typically such filters exhibit substantial surface area and/or roughness that can cause particle damage in biological suspensions, e.g., RBC hemolysis and platelet activation in blood.

Separation of biological fluids using a filter membrane with a nominal pore size is also common. For example, it is widely known that a filter membrane having 0.22 micron nominal pore size can be used to filter out assorted bacteria and the like from a liquid. Such membranes, also sometimes called capillary pore membranes, are available in polyester and polycarbonate material from, e.g., Nuclepore Corporation, and in polysulfone from Gelman Sciences, Inc. Such filter membranes have also been used to filter the cellular components of blood (sometimes called the "formed" components) from liquid plasma, i.e. "plasmapheresis."

While these membranes have worked satisfactorily in certain applications, such filter membranes have only a nominal pore size, as distinguished from pores of precise and consistent size, shape, and relative spacing to one another. Indeed, it is not uncommon for such nominal pore size membranes to include "doublets" (i.e., overlapping, non-conforming pores) which would allow passage through the membrane of particles larger than the nominal pore size. To be useful in performing procedures in which particles in a solution are "cleansed" of undesirable particles, the undesirable particles being several times larger than the desired particles, filter membranes must exhibit virtually no doublets.

The occurrence of doublets in prior art filter membranes, due to their fabrication techniques, has forced a compromise in their design. Specifically, in order to keep the occurrence of doublets to an acceptable low level, the mean pore-to-pore spacing must be relatively large, which limits the porosity (i.e., the ratio of the total pore area to the total membrane area) of these prior art membranes to about 7% and less. Generally, a lower porosity results in a lower flow rate through the filter membrane. Thus, although a filter membrane having a nominal pore size is suitable for defining an average or nominal maximum particle size that passes through the filter membrane, such membranes are not precisely sized to permit selective filtration of particles of comparable size based on other unique characteristics such as shape or deformability, and have significant drawbacks that limit their application.

A further difficulty with membrane separation of biological and other fluids is impairment of flow through the membrane due to the fouling or clogging of the filter membrane. Such fouling or clogging generally results from the deposition on the surface of the filter membrane of particles too large to pass through the membrane and plugging of the pores. Various methods are known for reducing or preventing the clogging of such membranes. For example, U.S. Pat. No. 5,194,145 to Schoendorfer, herein incorporated by reference, discloses a "couette flow" filter system in which the extraction of filtrate is accomplished through a membrane mounted on a cylindrical rotor within a stationary cylindrical cell. The relative movement between the two concentric cylinders generates a surface velocity that establishes vigorous vortices at the surface of the rotor. These vortices, called Taylor vortices, constantly sweep the membrane surface to limit cell deposition, while continuously replenishing the medium to be filtered.

A different technique to reduce membrane fouling is disclosed in U.S. Pat. No. 4,735,726 to Duggins, herein incorporated by reference. This patent discloses a method and apparatus for carrying out plasmapheresis by conducting blood over the surface of a microporous membrane in reciprocatory pulsatile flow by a peristaltic oscillator or other suitable pump for causing reciprocatory pulsations.

More specifically, Duggins discloses a filter housing having a blood flow region between two plasma flow regions. A central blood inlet port is connected to the blood flow region of the housing, while a blood collection channel is connected to a plasma-depleted blood outlet port, and a plasma collection port is connected to a plasma outlet port. A pair of membranes is disposed between each plasma flow region so that there is a blood flow path between the membranes. Blood is conducted in a forward direction (i.e., away from its source) over the first surface of each filter membrane by, e.g., a rotary peristaltic pump, a piston or syringe-pump, or a plunger or hose pump. Blood flow is pulsed in a reciprocatory fashion by a peristaltic oscillator connected to the housing through ports connected to areas near the end of the flow path. As a result, blood can be conducted in the forward direction and in a reverse direction over a first surface of each membrane at a net positive transmembrane pressure, while reducing the transmembrane pressure during the forward and reverse conduction of the blood. The frequency and volume of the reciprocatory pulses are selected to maximize the flow of plasma through the membranes without causing extensive blood trauma. The plasma which passes through each membrane is collected, while the plasma depleted blood is recirculated to the blood flow region.

More recently, it has been possible to make microporous filter membranes with pores having precise size and shape through techniques such as those shown in U.S. application Ser. No. 08/320,199, entitled "Porous Microfabricated Polymer Membrane Structure", filed Oct. 7, 1994, having the same assignee as the present invention and which is incorporated herein by reference. The aforesaid application generally discloses a process for microfabricating precise membranes using etchable polyimide film on a silicon substrate. A polymer film layer is made from a photoimageable polyimide material. The film is processed using negative photoresist techniques or etchable membrane fabrication technique to create a predefined geometric pattern of holes and intermediate spaces defining strands.

Alternatively, other processes, such as positive photoresist techniques, RIE (Reactive Ion Etching), LIGA (an abbreviation of the German for lithographic, galvanoformung, abformung, or in English, lithography, electroforming, and molding), may be used to create filter membranes with extremely small pore size (e.g., less than 10 microns) and having virtually zero doublets that are exceptionally uniform, with a high degree of consistency from one pore to the next. Further, electron beam and ion etch techniques also are possible means to produce precision, high porosity membranes with exceptionally small pores. With the doublet problem essentially eliminated by these various fabrication techniques, organic membrane structures with very high porosities (exceeding 35% and potentially achieving 80%) can be generated with the pore area limited only by structural considerations.

SUMMARY OF THE INVENTION

It is a general object of the invention to provide an improved method and apparatus utilizing precise pore size and shape membranes for selectively separating the particles or components in a medical, biological or other suspension based on the size, shape, deformation characteristics, or other unique characteristic of the various components to be separated.

More specifically, it is an object of the present invention to provide an improved method and apparatus for selectively the various components of whole blood, such as red blood cells, white blood cells, and platelets, or substances that may be found in whole blood, based upon their size, shape, and/or deformation characteristics.

It is a further object of the invention to provide method and apparatus employing precise pore size which include means for preventing fouling or clogging of the surface of the filter membrane.

These objects, as well as others which will become apparent upon reference to the following detailed description and accompanying drawings. Before turning to the detailed description, and for purposes of summary only, one aspect of the present invention is embodied in a method for separating a suspension comprising at least two types of particles, which are differently sized or shaped. Such particles may be biological. cells or cellular components and, more particularly, animal cells or cellular components characterized by having a non-rigid cell membrane, free of a rigid outer cell wall, and consequently being subject to trauma when stressed. The first type of particle may also be, but is not necessarily, deformable at a relatively lower force and/or faster rate than the second type of particle. This method comprises providing a filter membrane having substantially precisely dimensioned pore sizes, with the pores being dimensioned to allow passage of the first type of suspended particle without distortion or with only minimal distortion and passage of the second type of particle only with substantial distortion. Because the filter membrane has precisely dimensioned pores, with the spacing between the pores being maintained despite the smaller interval between the pores, the porosity of the membrane may be much greater than nominal pore size membranes, with less internal pathway variability. This faster filtration rates and/or smaller membranes for a given filtration rate, reducing the exposure time of cells within the shear environment of the separator and, consequently, reducing particle damage (such as WBC damage, platelet activation, and/or RBC hemolysis). Similarly, the smooth membrane surface and the smoothness of the internal pathways of the pores permit more consistent fluid shear near the membrane surface and further reduces the exposure time of the particles to the pores.

In this method, the membrane is contacted with the suspension to allow the passage of the first type of particle and to block passage of the second type of particle. To enhance the passage of the first type of particle through the pores, in one class of embodiments the membrane thickness may be small relative to the first type of particle. In another class of embodiments the membrane thickness may be large relative to the second type of particle in order to further inhibit deformation of the second type of particle. To enhance passage of the first type of particle and blockage of the second type of particle, the time that the suspension and membrane are in contact, the force of contact between the suspension and membrane and/or the relative movement between the suspension and membrane may be selectively varied, either alone or in combination.

In accordance with another aspect of the present invention, a method may be provided for filtering a suspension comprising at least two types of differently sized and/or shaped particles that differ in deformability characteristics. In this method, the filter membrane has substantially precisely dimensioned pores and may also have a very high porosity. The suspension and the precise pore size filter membrane are brought into contact with each other with a force or for a time sufficient to allow deformation of the first type of particle for passage through the pores, but insufficient to allow deformation of the second type of particle for passage through the pores.

Although the two aspects or methods above are referred to separately, they are not necessarily separate and may be employed in combination. For example, it is within the scope of the present invention to employ a precise pore size membrane that has precise size, and wherein the solution to be filtered includes first and second types of particles of different shape and different deformation characteristics. The precisely dimensioned pores may be of a shape conforming generally to the shape of the first particle only and of a size that requires some deformation of the first particle to pass therethrough. The suspension is brought into contact with the membrane for sufficient time and/or pressure to allow the first particle to deform and pass through the pores, but not the second particle. As in the first-described method, the time that the suspension and membrane are in contact, the force of contact between the suspension and membrane and/or the relative movement between the suspension and membrane may be selectively varied, either alone or in combination, to enhance passage of the first type of particle through the membrane.

In the methods referred to above, the lack of non-conforming pores improves the purity of separation and the very high available porosity improves the process by reducing the suspended particles' exposure time in the filtration shear field, as the particles pass through the membrane, by a factor of about 3 to 11, thus reducing the trauma to the separated particles due to filtering. The required membrane area is reduced by a similar factor, thus potentially reducing device size and cost substantially, and reducing particle stress related to the time of exposure of the particle to the shear field.

In the methods described above, an additional step of cleaning the upstream surface of the membrane may be included to prevent accumulation of the second type of particle on the surface of the membrane, which may result in clogging or blocking of the pores. By way of example, and not limitation, the cleaning step may be performed by flowing suspension across, i.e., parallel to, the surface of the filter membrane, creating turbulence on the surface of the membrane to sweep the clogging particles off the surface, or relatively oscillating the membrane and suspension to flush the second type of particles off the surface of the membrane.

The present invention is also embodied in apparatus for carrying out the above methods. An apparatus for performing the first mentioned method, for example, may comprise a filter membrane having substantially precisely dimensioned pores (which includes membrane thickness requirements), shaped to correspond substantially to the shape of the first type of particle and to allow passage thereof without or upon only minor deformation of the first type of particle, but to block passage of the second type of particle. Means is provided for bringing the suspension and the membrane into contact sufficient to permit passage of the first type of particle through the membrane, but insufficient to allow for substantially any of the second type of particle to pass through the membrane pores. The aforesaid means may also reduce clogging of the membrane pores.

Apparatus for performing the second identified method may also comprise a filter membrane having substantially precisely dimensioned pores (which includes membrane thickness requirements). In the second embodiment, the membrane pores are precisely dimensioned to allow passage of the first type of particle only upon deformation and the first type of particle is deformable at a faster rate than the second type of particle. Like the apparatus for performing the first method, the second apparatus also includes means for bringing the suspension into contact with the membrane with a force—either direct or shear—and for a time sufficient to permit the first type of particle to deform and pass through the membrane, but insufficient to allow deformation of substantially any of the second type of particle for passage through or plugging of the membrane pores. Of course, great care is necessary in the selection of membrane materials for separation, concentration, or removal of particles from suspension, particularly in the case of biological suspensions such as blood. Hydrophilic materials, such as polycarbonate, or special surface coatings or modifications, in addition to anticoagulants, are typically required for blood products to avoid or minimize platelet activation, blood cell aggregation, clotting, and/or hemolysis.

As set forth more fully below, these methods and apparatus find particular application in the selective separation of the formed elements of blood (red cells, white cells and platelets) from one another or the separation of formed components from the plasma, the liquid in which they are suspended. If, for example, in the first method and apparatus the liquid to be separated is whole blood, and it is specifically desired to separate the white blood cells from the red blood cells, a filter membrane may be provided that has pores precisely rectangularly dimensioned to measure approximately 1.8 microns to 3.5 microns by approximately 6.0 microns to 14.0 microns to allow passage of red blood cells without deformation or with only minor deformation and white blood cells only upon substantial deformation of the white blood cells. It is known that white blood cells deform at a substantially slower rate than red blood cells when subjected to the same force. The whole blood and filter membrane are brought into contact for a time sufficient, or with a force sufficient, or a combination of time and force sufficient, to allow any required deformation of the red blood cells for passage through the pores in the filter membrane, but insufficient to deform substantially all of the white blood cells for passage through the pores.

The description above is intended only by way of summary. A more detailed description of the various features and advantages of the present invention are set forth below.

BRIEF DESCRIPTION OF THE DRAWINGS

FIGS. 12a–c show the relative sizes of various blood cells with respect to prior art track-etched membranes.

DETAILED DESCRIPTION OF THE PREFERRED EMBODIMENTS

Figure 1:
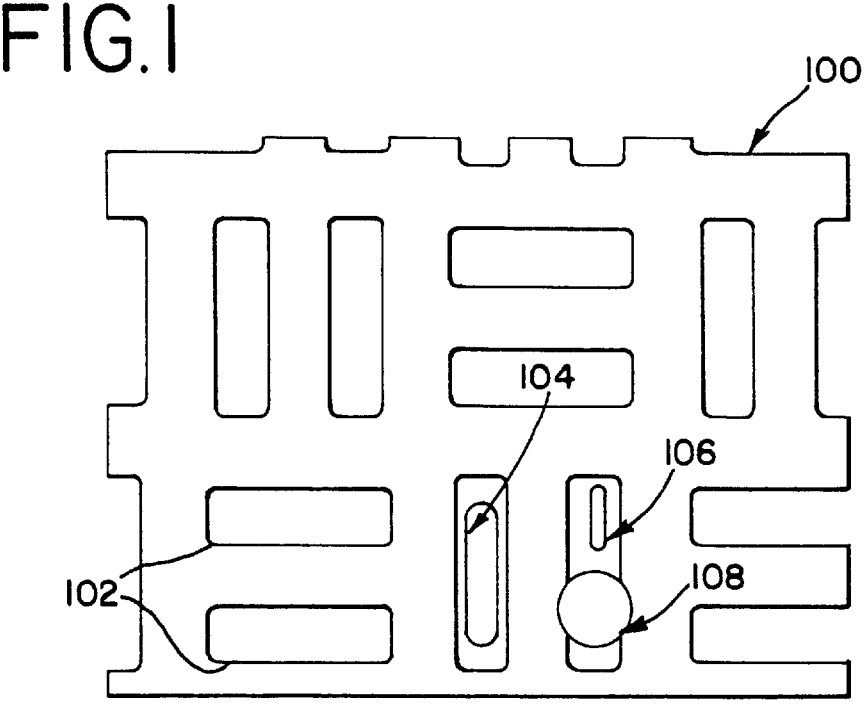
FIG. 1 is a plan view of a portion of a precise pore plastic membrane according to the present invention in which the pores are oval or rectangular in shape, are arrayed in an alternating pair pattern and, by way of example, may measure 2.5 microns by 9 microns, while also illustrating the discrimination of such pores based on the sizes of various blood components.

Turning now to the figures, and beginning with FIG. 1, the present invention is generally embodied in a system or apparatus employing a filter membrane 100 having precisely dimensioned pores 102, of a particular size and/or shape that may be selected depending on the suspension or other fluid to be filtered. As used herein with reference to membrane pore size, "precise," "precisely dimensioned," or variants thereof means pore sizes that are substantially of a selected size and shape, typically but not necessarily less than about 10–20 microns and as small as 0.1 microns and smaller, with thicknesses typically but not necessarily less than about 1 to 15 microns.

The membrane employed in the present invention may be of polymeric material such as polyimide material and may be made in accordance with the method set forth in the above-identified U.S. patent application Ser. No. 08/320, 199. Generally, moldable materials, such as thermoplastics, optimized to render surfaces slippery to the suspension media and particles, are appropriate for the separation of blood components. Medical grade polycarbonate may be formed by methods such as LIGA. Alternatively, for applications involving hydrophobic suspensions, e.g., the reclamation of petroleum based suspensions such as transmission fluid, a precise pore size and shape membrane made of a hydrophobic material would be appropriate. Precise pore size membranes of other materials or made in other ways, whether previously known or hereafter developed, are within contemplation of the present invention.

Although depicted in the context of blood filtration or separation, the present invention is not limited to that particular application. FIGS. 1–5, for example, show various embodiments of a precise pore size membrane that may be employed in the present invention. Such membranes may have either flat or curvilinear surfaces. FIG. 1 depicts a membrane 100 having a pattern of alternating pores 102. The illustrated pores 102 are generally rectangular in shape, with a length of 9 microns and a width of about 2.5 microns. The spacing between the pores 102 may be as small as dimensional tolerances and strength of the membrane material permit, allowing porosity to be maximized for a given material and application.

The shape and size of the precise pores and the spacing between the pores may be selected depending on the desired application. The rectangular or oval pore shape and size depicted in FIG. 1 are believed to be particularly useful in separating leukocytes from red cells, platelets and plasma components of human blood. (For the purposes of this application, "whole blood" shall also include anticoagulated whole blood and blood having diseases such as sickle cell anemia.) Mature normal human red cells, which have no nucleus, typically are of discoid shape, with a diameter of about 7 microns and a thickness of about 2 microns. Although not perfectly spherical, leukocytes or white cells typically have an outer diameter of a minimum of about 4.5 microns to about 20 microns, with a nucleus of typically 3.8 to 4 microns or greater. Platelets are much smaller than both red cells and white cells.

In accordance with the present invention, a precise pore size membrane filter having generally rectangular or oval shaped pores of about 9 microns×2.5 microns would allow red cells, platelets and plasma to pass therethrough but substantially prevent white cells from passing through. This is illustrated in FIG. 1, which shows a red cell 104 passing through a pore 102 edgewise, a platelet 106 passing through a pore, and a leukocyte 108 being blocked from passage by reason of the small width of the pore 102, which is smaller than the size of the white cell or its nucleus.

Figure 2:
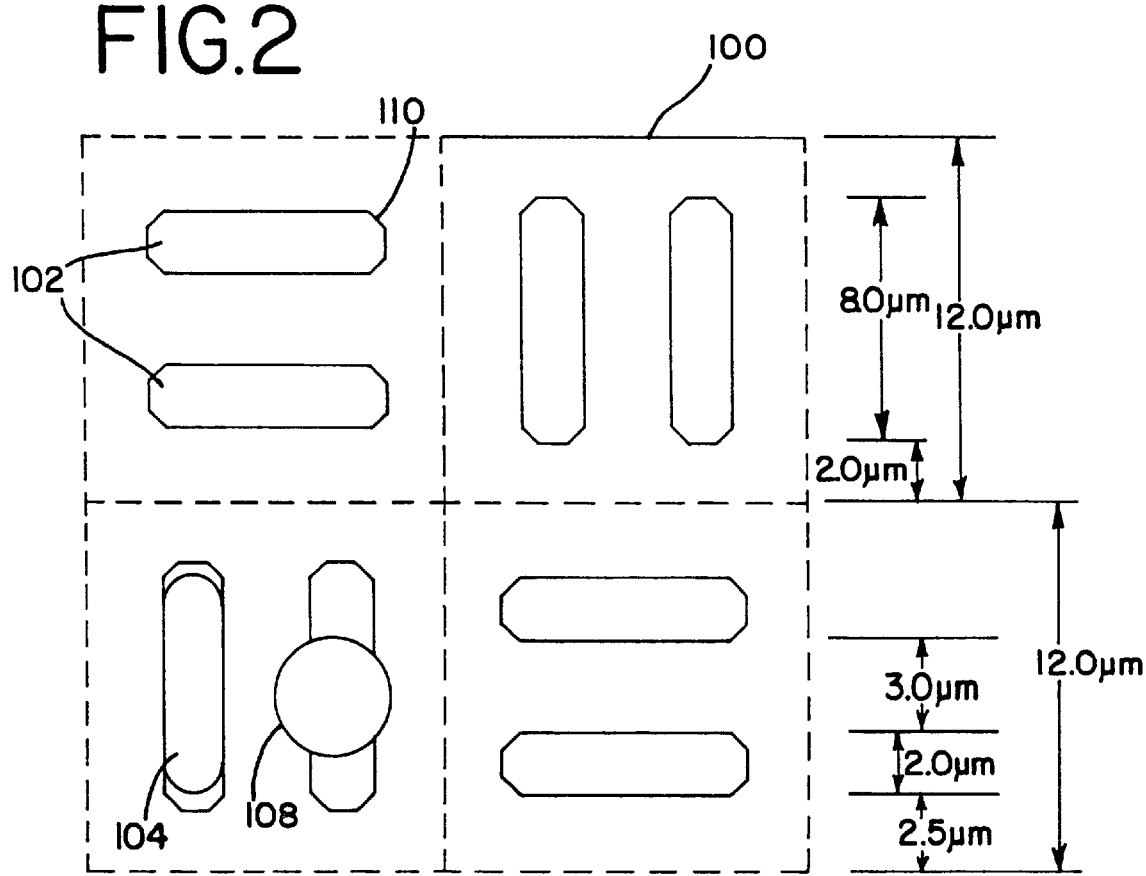
FIG. 2 is a plan view of a precise pore filter membrane similar to FIG. 1 in which the pores, by way of example, may measure 2 microns by 8 microns.

FIG. 2 shows a membrane 100 having a similar alternating pattern of precise pores 102, with essentially rectangular pores of about 8 microns length and 2 microns width. Spacing between adjacent pores 102 is from about 3 to 4 microns. Very small fillets 110, such as 0.5 microns×0.5 microns, are provided in each corner of the pore to reduce stress concentrations and prevent excessive or unnecessary plasma flow through the pores. While the corner fillets 110 make the pores 102 "oval," for the purposes of this application such oval pores are considered to be substantially rectangular. A red cell and white cell are illustrated, respectively, passing through a pore and being blocked by a pore.

Figure 3:
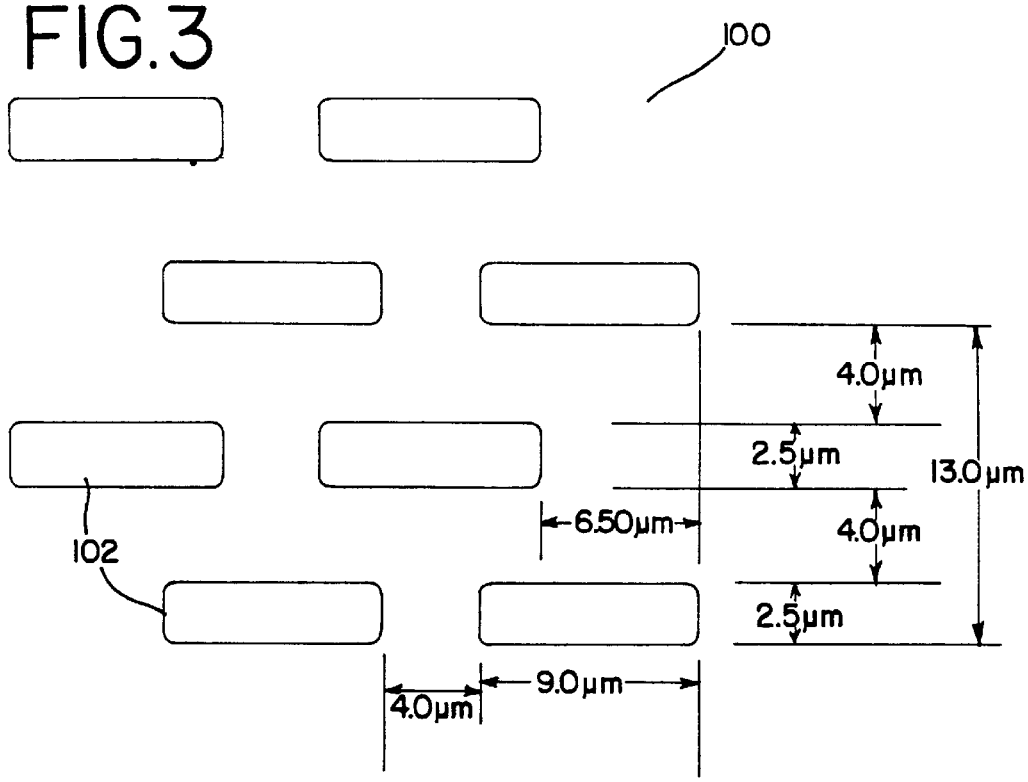
FIG. 3 is a plan view of a precise pore filter membrane similar to FIG. 1, except that the pores are arranged in an overlapping unidirectional relationship and, by way of example, may measure 2.5 microns by 9 microns.

As noted above, the size and shape of the precise pores may be selected depending on the desired application. The same may also be said of the pattern of pores. FIG. 3 shows a filter membrane 100 similar to FIG. 1, except that the pores 102 are arranged in a parallel overlapping unidirectional relationship. This arrangement may increase the probability of proper RBC alignment for certain separator means, such as rotating membrane devices, whereas the alternating pore pattern may increase the probability of proper alignment of RBCs in other filter devices, such as oscillating cross-flow systems, which will be discussed in more detail later.

Figure 4:
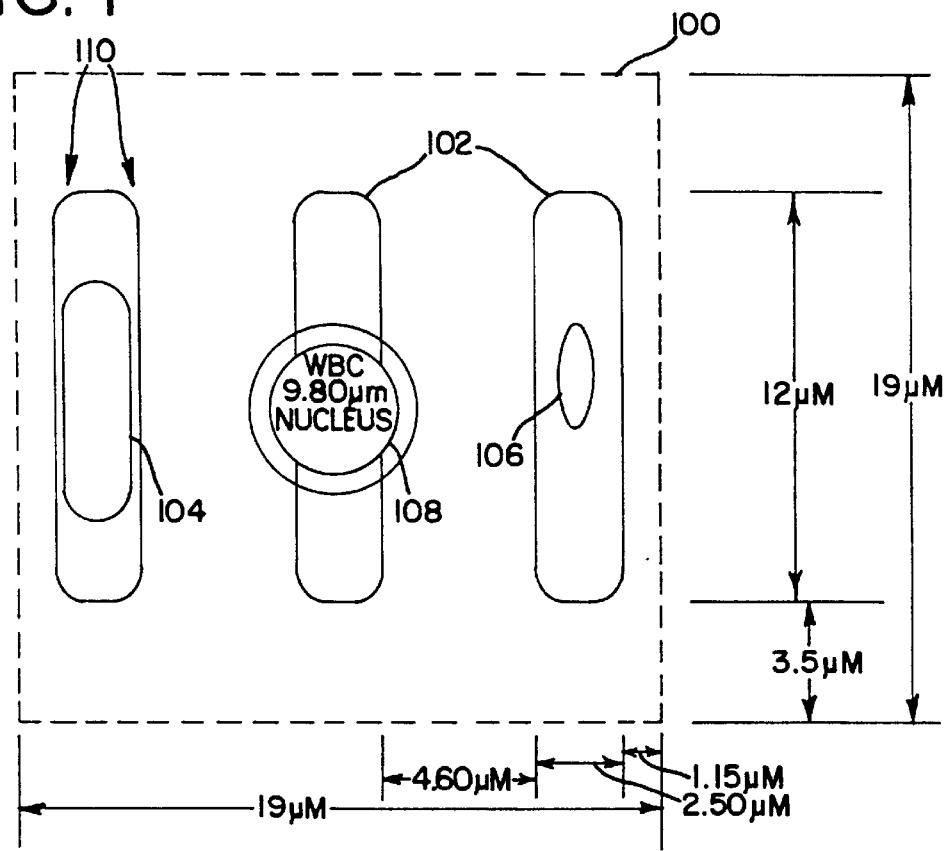
FIG. 4 is a plan view of a family of precise pore filter membrane similar to FIG. 3 in which, by way of example, the pores measure 2.5 microns by 12 microns, and illustrating the passage of a red cell and the blockage of a white cell.

FIG. 4 depicts a family of membranes 100 having pores 102 of generally rectangular or, due to the corner fillets 110, somewhat oval shaped, about 12 microns long and 2.5 microns wide. While only a single block of three pores is illustrated in FIG. 4, a membrane 100 may have such blocks arranged with the major axis of the pores in both directions, like the membranes illustrated in FIGS. 1 and 2. It is contemplated that a width of the rectangular pore 102 up to about 3–3.5 microns will be narrow enough to generally block the passage of leukocytes. The membrane 100 may be of a variety of thicknesses, such as 1.0±0.1 microns, 3.0±0.3 microns, 5.0±0.3 microns, or 10.0±0.5 microns, which is one parameter of the precise size and shape of the pores. of course, the closer the width of the pores gets to the diameter of the white cell nucleus, which is about 3.8 microns minimum, and to the overall diameter of white cells which may be about 5 microns minimum, the greater the possibility of white cells passing through the membrane.

Figure 5:
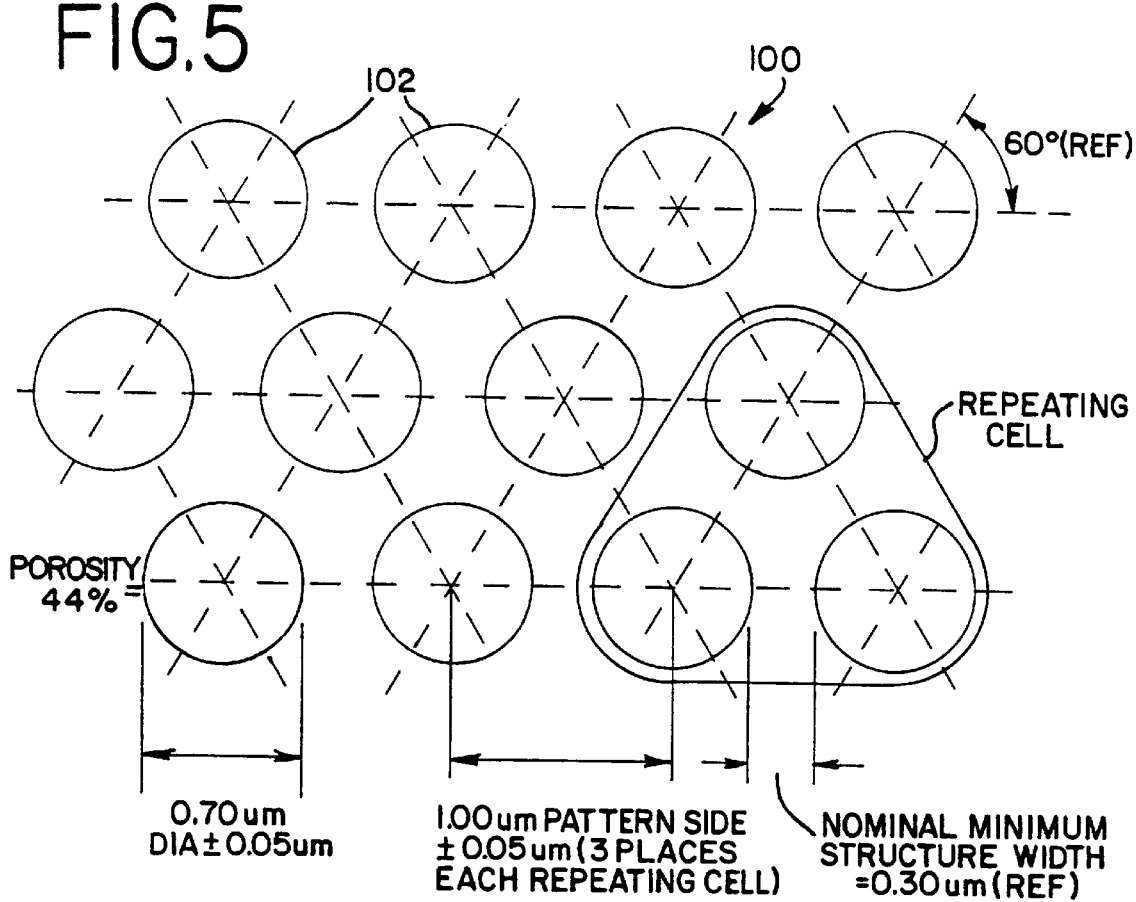
FIG. 5 is a plan view of a very high porosity precise pore 30 filter membrane with dimension tolerances for filtering plasma from whole blood with alternating rows of circular pores in which, by way of example, the pores measure about 0.70 micron in diameter.

FIG. 5 illustrates a precise pore size membrane 100 having precise pores 102 that are essentially circular, which may be used, for example, in single particle (e.g. blood cell) concentration and washing applications, and in suspension media collection applications, such as collection of plasma from whole blood wherein platelet-free plasma is considered a media (including exceptionally small suspended proteins negligibly small with respect to these membrane pore sizes). Such a process is termed "suspension concentration," whether the desired product is either the concentrated particle suspension or the substantially particle-free media filtrate, or both. The packing density of pores has been optimized to provide a uniquely high porosity, achievable through the precise dimensioning and tolerancing of the pores. This membrane provides a porosity of about 56%, approximately eight times that of prior art track etch membranes. This eight-fold increase in porosity provides the potential for greatly increased filtrate flow rates, or greatly reduced shear forces for equivalent filtrate flow rates, or greatly reduced membrane areas for reduced separator costs. The reduction in membrane area significantly reduces the cell exposure time in high-shear couette flow separators, reducing cell stress, platelet activation, and RBC hemolysis.

Membranes of the type illustrated in FIG. 5 may be optimized for low pressure loss within membrane pores by maximizing the precisely dimensioned pore size up to a size allowing free media flow through the pores, while allowing substantially no particle deformation, in order to inhibit particle passage through the pores. Precisely dimensioned pores have pore size and size tolerances and pore-to-pore spacing and spacing tolerances to insure against non-conforming pores (doublets). While various pore width ranges, length ranges, and thickness ranges have been disclosed, many interrelated parameters, in addition to specific particle size, shape, and deformability characteristics, must be considered in membrane dimension optimization. Such parameters include filtrate flow rates (affecting contact pressure), concentrate flow rates and RPM (affecting exposure time of a cell over a pore, and shear forces), membrane thickness, stiffnesses, viscosities, surface characteristics, and the plasma or media boundary layers, both with respect to the overall membrane and separator, and adjacent the inner surfaces of the pore walls, necessary to aid transport of (and to lubricate) RBCs so that they can pass easily through the pores without plugging (clogging) the membrane or damaging the cells. Deformation and lack of substantial deformation of suspension particles includes three-dimensional geometries, pressures, forces, and local flow patterns.

Although the figures discussed above have been shown for separating particles by reason of their size and/or shape, in accordance with another aspect of the present invention, the relative deformability of the particles in the solution may be taken into account to enhance filtration. For example, it is known that in human blood material, normal red cells are relatively more readily deformable than white cells and deform faster and under less force than the white cells, whereas, given sufficient time, WBCs can undergo great deformation and actually pass through minute vascular openings.

In the article Rheology of Leukocytes, Chien, et al., Annals of The New York Academy of Sciences, UMI Article Clearing House, Vol. 516, 1987, Chien reports on investigations of large deformations of WBCs by studying their filterability through polycarbonite sieves with 5 micron pores and concluded that the results are affected by both the geometric and intrinsic Theological properties of the cell. Below is a table reproduced from Chien et al. comparing the Theological and geometric properties of human erythrocytes (RBCs) and neutrophils (WBCs):

|  | Erythrocytes | Neutrophils |
| --- | --- | --- |
| Cell volume ($\mu m^3$) | 90 | 190 |
| Surface area ($\mu m^3$) |  |  |
| Measured | 140 | 300 |
| Calculated for sphere with same volume | 97 | 160 |
| Excess surface area ($\mu m^2$) | 43(44%) | 140(88%) |
| Minimum cylindrical diameter ($\mu m$) | 2.7 | 2.6 |
| Deforming stress needed for |  |  |
| $D_{pm}/R_p = 3$ (dyn/cm) | 0.025 | 0.10 |
| Time constant for small deformation (ms) | 20–120[a,b] | 650 |
| Cellular viscosity (poise) | 0.7 | 130 |

Chien et al. indicate that the geometric relationship between cell volume and membrane area of WBCs is such that they should be able to deform to pass through as narrow a channel as the RBCs. However, Chien et al. found that WBCs had a relative inability when compared to RBCs to traverse a 5 micron channel and attributed this mainly due to the difference in their viscoelastic properties. The short term deformation resistance of WBCs is four times that of RBC's, and the cellular viscosity of WBCs is more than 150 times higher than that of RBCS. Further, WBCs have nuclei which are less deformable than the cell cytoplasm, while mature RBCs have no nuclei. Chien et al. believe that their results illustrate the potential importance of increased WBCs in causing microvascular obstruction.

In accordance with one aspect of the present invention, a fluid pressure or transmembrane pressure is provided and a pore size and shape are provided to allow RBCs to pass relatively freely or with some deformation, while forcing WBCs to deform to a greater extent. The thickness of the filter membrane is inversely related to both the transit time and force required to deform a WBC or RBC so that it can pass through the filter membrane. The filter membranes employed in the instant invention are on the order of about 1 to 15 microns thick. Since the WBC deformation occurs 10–50 times slower than RBC deformation, in membranes such as those described above, which have pore widths substantially smaller than the diameter of a white cell, the WBCs must remain at the entry to the pores for a finite time before they might fully enter and become engaged with the membrane. By selecting the fluid shear rate and exposure or contact time and/or pressure between the source suspension and the membrane, red cells may be allowed to deform and pass through, while white cells, which have greater resistance to deformation, are substantially filtered out.

Figure 6:
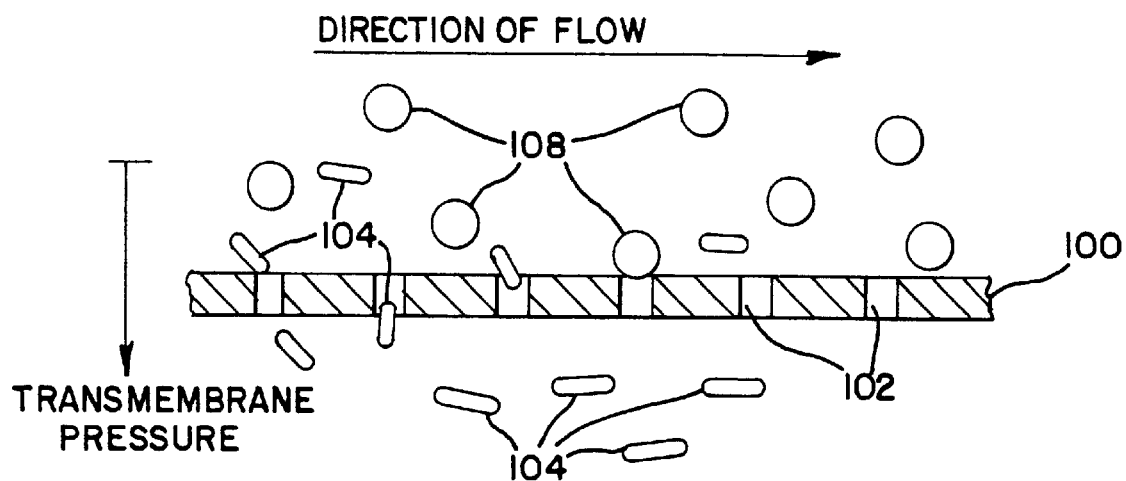
FIG. 6 is a diagrammatic cross-sectional view of a precise pore filter membrane with a shear flow of blood across its surface and a positive transmembrane pressure.

There are various techniques for controlling the time that the solution and membrane are in contact, and/or for controlling the relative pressure between the solution and membrane. FIG. 6, for example, illustrates, in cross section, a filter membrane 100 with unidirectional precise pores 102 (such as those shown in FIG. 3), showing the widths of the pores 102. Solution comprising red cells 104 and white cells 108 is shown flowing transversely across the surface of the membrane. The relative speed of the solution over the surface of the membrane 100 is one method of determining or varying the contact time between the solution and the membrane. In other words, by using a high relative velocity between the membrane 100 and solution, only a small amount of time is available for cells to pass through the precise size and shape pores. This aids in allowing, for example, red cells 104 to pass through the membrane but not allowing sufficient time for white cells 108 to deform to enter the pores before they are swept away by the shear force exerted by relative movement of the liquid across the membrane.

Figure 7:
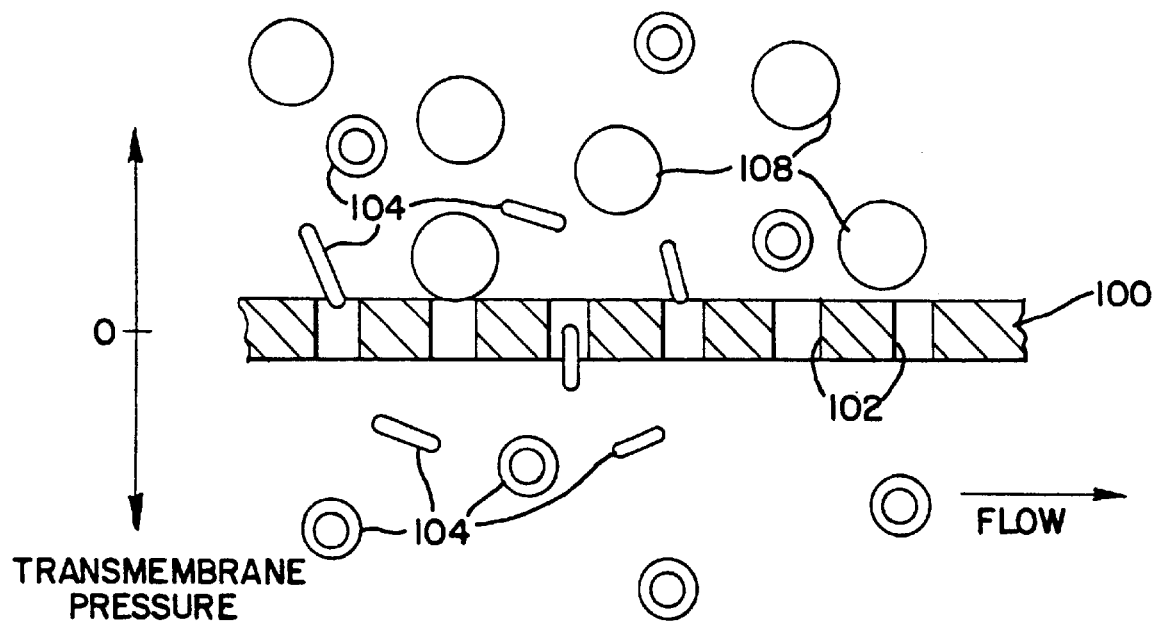
FIG. 7 is a diagrammatic cross-sectional view of a precise pore filter membrane in which the transmembrane pressure is varied, such as by oscillating positively and negatively.

Another way to optimize the passage of one particle and to block the passage of other particles based on different deformability rates is to vary the transmembrane pressure between the upstream and downstream sides of the membrane, as illustrated generally in FIG. 7. This may be accomplished, for example, by oscillating the membrane 100 relative to the suspension to be filtered or by varying the pressure of the suspension. Relative oscillation of the membrane 100 toward and away from the solution or vice versa would allow, for example, the particles that are relatively quickly deformable or that require little deformation, such as red cells 104, to pass through the membrane 100, while the less deformable particles, such as white cells 108, do not have sufficient time to deform to engage the membrane or pass through the pores 102 before the relative oscillation moves the less deformable particles. The particles that have passed through the pores 102 may be removed from the region adjacent the membrane 100 by, e.g., flow parallel to the membrane surface. A steady flow parallel to the surface of the filter membrane can be maintained by a pump, while reciprocatory flow perpendicular to the filter membrane can be created with, e.g., piezoelectric devices, to provide an appropriate maximum contact time between the WBCs and the filter membrane so that WBCs do not pass through the membrane.

Another method for ensuring that the WBCs do not remain in contact with the filter membrane for a period of time sufficient for them to either deform sufficiently to pass through the membrane or to merely clog or foul the filter membrane include sweeping the membrane with high shear flow, such as Taylor vortices (as disclosed in Schoendorfer in connection with a rotary filter), or having a reciprocatory pulsatile flow (as disclosed in Duggins).

Relative oscillation and relative shear flow between the suspension and membrane may also be used in combination to enhance passage of the desired particles or cells and to prevent accumulation of particles or cells removed from the suspension. For example, the continuous retention of WBCs near the upstream side of the filter membrane will form a leukocyte-rich blood layer near the membrane and may ultimately overcome the ability to keep the orifices clean of WBCs. The leukocytes that form a WBC-rich layer can be swept away from the membrane surface by any number of methods including, e.g., by flowing the feed blood tangentially across the membrane as discussed above or by relative oscillatory movement of the membrane and suspension. In addition, as plasma is drawn through the membrane, the WBC concentration increases, potentially contributing to membrane clogging. The WBC concentration can be lowered by introducing a diluent or wash fluid, such as blood plasma or other media, at one or more input taps along the filter device.

The Chien et al. article indicates that a circular orifice area that discriminates between RBCs and WBCs is in the 6–15 micron$^2$ range, based on the observation that a 6.9 micron diameter pore membrane passed blood freely; while membranes with a 4.5 micron diameter pores pass blood with a slowly increasing pressure as a result of progressive plugging of pores; and a 2.6 micron diameter pore membrane initially plugged with WBCs. As a consequence, it is believed that pores measuring approximately 1.8 microns to 3.5 microns by approximately 8.0 microns to 12.0 microns will pass RBC's therethrough, but retain WBCs, under appropriate combinations of flow rates, RPM, and transmembrane pressure (for a couette device), or tangential-flow rate, pulsatile frequency and amplitude, and transmembrane pressure (for a Duggins device), for the specific source suspension (e.g., whole blood, buffy coat, or low hematocrit suspensions in cell washing applications).

Automated control systems for controlling the exposure time and force of blood suspensions against microporous membrane in rotating filter devices are shown in U.S. Pat. Nos. 4,879,040, and 5,069,792, to Prince, et al., and U.S. Pat. No. 4,994,188 to Prince, all having the same assignee as the present invention. These systems are used in automated apheresis to measure membrane flow resistance of the disposable filter to the donor plasma, and define control curves (U.S. Pat. No. 4,879,040), control RPM values (U.S. Pat.. No. 4,994,188) and control surfaces (U.S. Pat. No. 5,069,792) to maintain transmembrane pressure at a substantially maximum safe value for the source blood hematocrit, and the source and filtrate flow rates. This maximum safe value provides substantially maximum plasma throughput, while remaining within a reversible membrane plugging region (in which blood cells near membrane pores influence the pressure, but do not plug the membrane) and lower than an irreversible membrane plugging region (in which blood cells become entrapped in membrane pores and plug the membrane irreversibly) within the four dimensional plasma flow, pressure, RPM, and blood flow space.

Resistance to blood flow through filters with very small pores increases rapidly as the pore diameter decreases. Consequently, it is believed that "oval" or rectangular pores may have significant advantages over circular pores. An oval pore with a width small enough to prevent passage of WBCs has a significantly larger cross-sectional area than a circular pore that is small enough to prevent the passage of WBCs. As a result, while the resistance to flow of suspended RBCs may be much lower for oval pores than for circular pores, the local pressure upon a WBC may be reduced.

The filter membranes 100 as shown in FIGS. 1–5 can be employed in many different filtration systems including static filtration, stirred filtration, cross flow filtration, vibrating filtration, and couette flow filtration.

Figure 8:
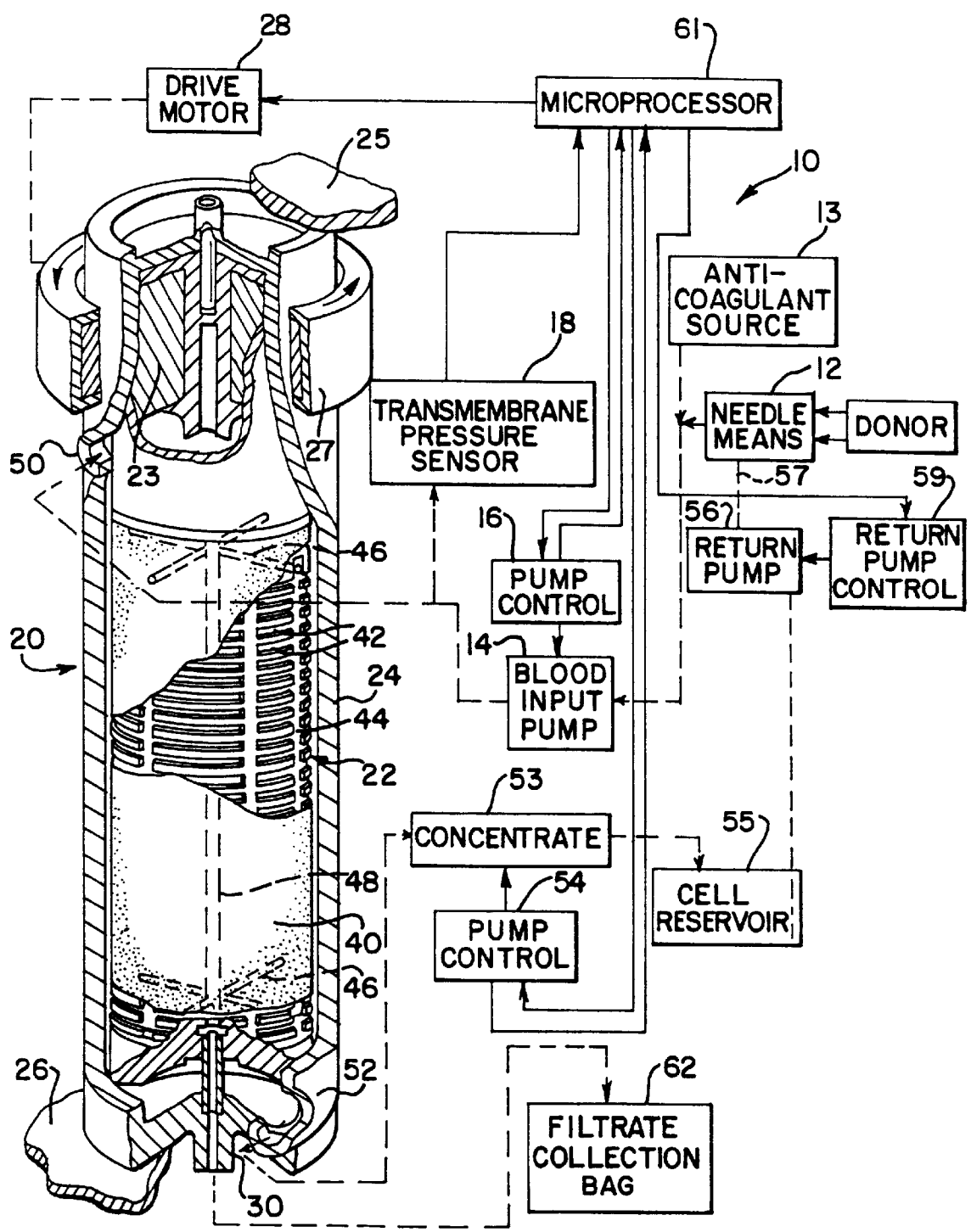
FIG. 8 is a perspective view in partial cross section of a rotary membrane filter of the type which is believed to be suitable for use in connection with the present invention.

A filter system 10 is shown in FIG. 8, in which the elements have been depicted only generally, provides an example of a blood separation apparatus in accordance with the present invention in the context of blood product collection in apheresis. Whole blood is taken from a donor via a needle 12. Disposable tubing is utilized to conduct the blood from the donor, and to combine it with a flow of anticoagulant from a source 13. An input blood pump 14, such as a peristaltic or pressure roller device, feeds the combined flow, when actuated by an associated blood pump control 16, to a transmembrane pressure sensor 18 and also to a disposable separator device 20.

The separator 20 is in the form of a rotor 22 having magnetic elements 23 integral with one end and rotatable about a central longitudinal axis within a stationary housing or shear 24. The rotor 22 is receivable between a pair of positioning supports 25, 26 spaced apart along the central axis. The upper support 25 provides a positioning seat for a non-rotating upper portion of the separator device 20. At the upper end, a magnetic drive 27 encompasses and is magnetically coupled to the magnetic elements 23 integral with the rotor 22, and is rotated by a drive motor 28. The lower support 26 receives the lower end of the stationary housing 24 and defines an opening through which a filtrate outlet 30 coaxial with the central axis may provide plasma as output, using a precise pore plastic membrane similar to that depicted in FIG. 5 for the separation of plasma from whole blood.

Figure 9:
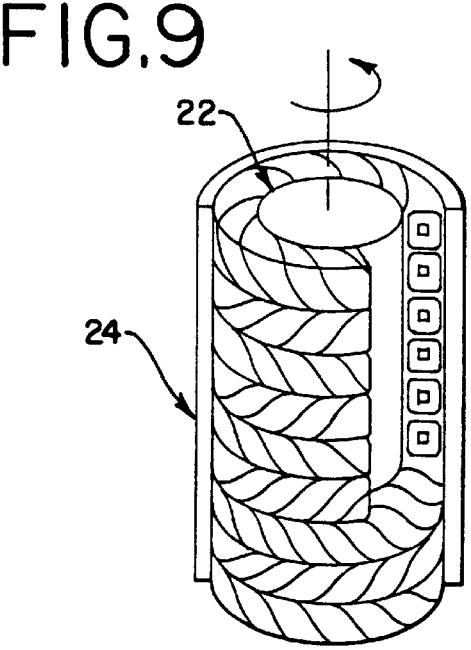
FIG. 9 is a perspective view in cross section of a rotary membrane filter of the type shown in FIG. 8 showing Taylor vortices in the gap between an interior rotor and an outer housing.
Figure 10:
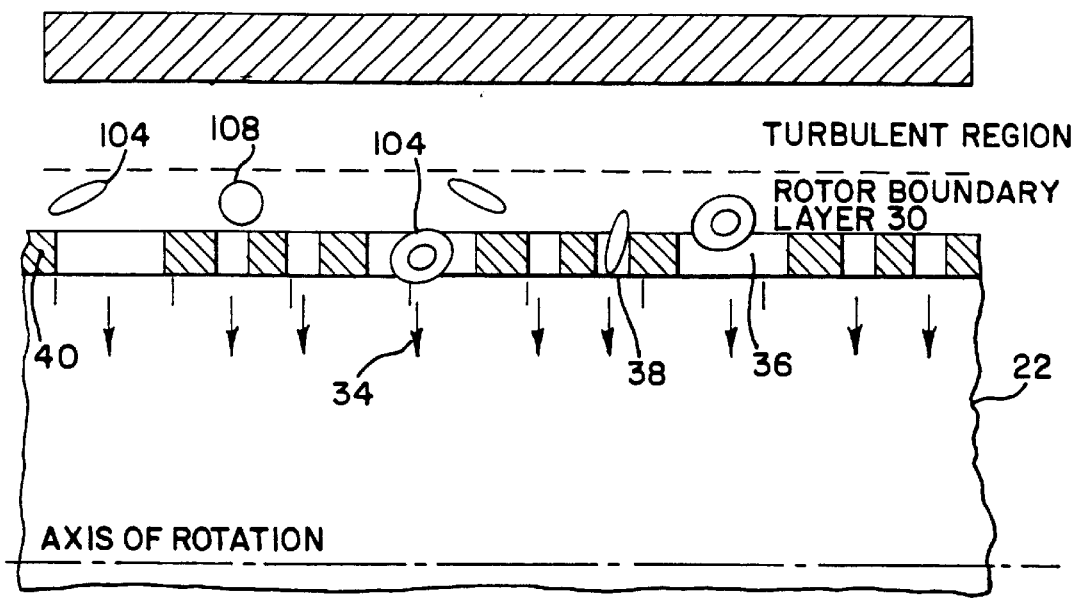
FIG. 10 is a cross-sectional view of the gap and membrane in FIG. 9 showing RBC orientations in the boundary layer and the tipping of RBCs to enter pores in the membrane.

Alternatively, the surface of the rotor 22 may be covered by a precise pore plastic filter membrane 40 of the type discussed above, such as that illustrated in FIG. 1, that has surface apertures in the range of approximately 1.8 to 3.5 microns by approximately 6.0 to 14.0 microns. The membrane 40 has a radius of curvature with its center coincident with the axis of rotation of the rotor 22. The filter membrane 40 may be provided with a polyester mesh backing material (not shown) to provide adequate support. It is believed that the shear, turbulence, and/or Taylor vortices (FIG. 9) created in the gap between the rotor 22 and the housing 24 will cause substantial mixing and "randomizing" of RBC alignment in that region. However, as illustrated in FIG. 10, a thin boundary layer 30 surrounding the membrane surface 32 may cause a preferential "planar alignment" close to the surface. This may be overcome by the radially inward filtrate flow 34. "Planar alignment" occurs when the planar surfaces of the discoid RBCs 104 are parallel to a plane tangent to the rotor surface 32. There may be, therefore, a preferred alignment of pores, employing a membrane design as in FIG. 3.

In one embodiment, the filter membrane 40 is preferably mounted on the rotor so that the major axis of the pores are aligned parallel to the axis of rotation of the rotor 22 (i.e., when the separator rotational axis is vertical, the major axis of the pores is vertical). This orientation of the pores may be advantageous due to the effect of the radially-inward flow forces that may tend to tip a leading RBC edge into the pore, identified as vertical pore 36. This may lead to the least radially-inward resistance to the RBC flow. However, the exceptionally complex nature of the flow patterns, Taylor vortices, fluid boundary layers, RBC dynamics, and influence of the inward radial flow complicate an analytical description. It may well prove best to orient the pore major axis normal to the spin axis, identified in FIG. 10 as horizontal pore 38 (in a second embodiment), or the alternating pore design (in a third embodiment) may be most effective, employing membranes as in FIGS. 1 and 2.

Under the membrane 40, the rotor surface is configured to define a plurality of circumferential grooves 42, interconnected by longitudinal grooves 44 which in turn communicate via radial conduits 46 with a central manifold 48. The manifold 48 is in communication, through an end seal and bearing arrangement (not shown in detail) with the filtrate outlet 30.

While blood from the donor is fed into the space between the rotor 22 and inner wall of the concentric housing 24 via a tangential source inlet 50 coupled by a flexible tubing (not shown in detail) to the blood input pump 14. A concentrate flow is taken from a tangential outlet orifice 52 spaced apart from the inlet along-the longitudinal axis of the separator device 20. Flexible tubing (also not shown in detail) couples the outlet 52, through a peristaltic pump 53 operated by a control 54, to a reservoir 55. The operation of separator 20 can thereby be isolated from the donor so that alternate pump and return cycles can be used with a single needle device. Concentrated WBCs are reinfused in the donor at the needle means by a return pump 56 in a return line 57 between the needle means 12 and the reservoir 55. A return pump control 59 operates the return pump 56 at rates and times determined by the control system, which may include means for sensing the level in the reservoir 55.

The separator device 20 extracts RBCs (and platelets and plasma) from the whole blood flow, through the membrane 40. RBCs and platelets flow through the membrane 40, into the circumferential and longitudinal grooves 42, 44 on the rotor 22 surface and then into the central manifold 48 via the radial conduits 46. The collected RBCs and platelets in the central manifold 48 pass through the filtrate outlet 30 to a collection bag 62.

Regardless of the method of filtration used, in order to obtain high flow rates through the filter, it is necessary to prevent clogging or fouling of the filter membrane by particles that are sized too large to pass through the pores, or by activated or clotting blood elements. Such clogging or fouling can be prevented, or at least minimized, by directing a flow of the suspension across the surface of the filter membrane as shown in FIG. 6. By way only of example, this can be accomplished by utilizing the apparatus disclosed in the Schoendorfer patent discussed above. Alternatively, the transmembrane pressure can be oscillated, as shown in FIG. 7, by employing a reciprocatory pulsatile flow, as shown in the Duggins patent, discussed above. Alternatively, the filter membrane itself can be oscillated.

Figure 11:
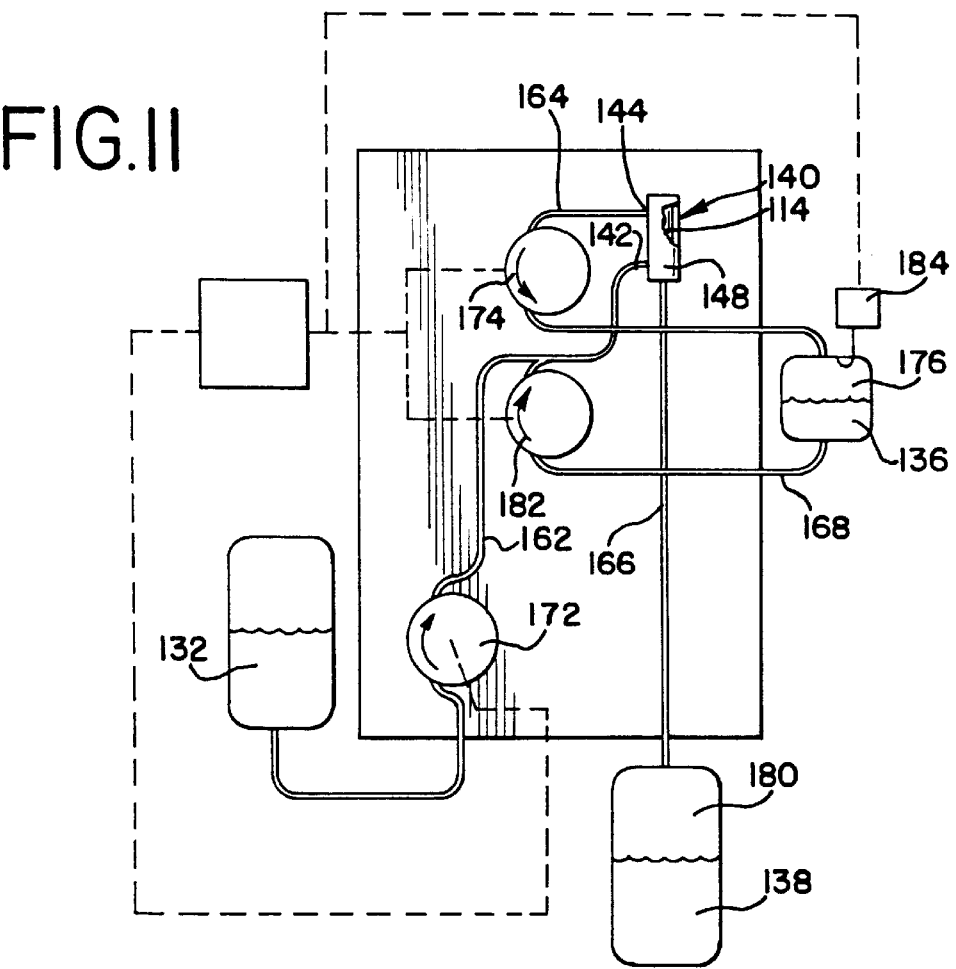
FIG. 11 is a schematic diagram of a cell washing apparatus of the type which would be suitable for use in connection with the present invention.

FIG. 11 illustrates a cellular suspension concentration system (similar to that disclosed in U.S. Pat. No. 5,234,608, which has the same assignee as the present invention and is incorporated herein by reference) that can advantageously utilize the invention of the present application. The '608 patent discloses a single cellular concentration, using platelet concentration, and has also been employed to separate or wash a suspension of a plurality of cell types (such as RBCs, WBCs and platelets) in order to isolate the WBCs, (i.e., wash out the platelets and RBCS) using, for example, 3.8 micron diameter track-etch membranes.

FIGS. 12*a–c* illustrate the approximate relative sizes of RBCs and platelets with respect to the smallest WBCs that are desired to be retained, and shows graphically that a 4.0 micron pore diameter (FIG. 12*b*)—which is necessary in order to substantially block all WBCs—exhibits high resistance to the flow of RBCs. 5.0 micron pores (FIG. 12*c*) each pass RBCs, but also easily pass small WBCs. Decreasing the circular pore size to 3.0 microns (FIG. 12*a*) generally blocks all WBCS, but also greatly inhibits passage of RBCs. This system provides another particularly suitable example for the application of the present invention, using, for example, the pore design of FIG. 4.

Looking again at FIG. 11, a quantity of mononuclear cell preparation 136 may be obtained, for example, from a donor or patient during an apheresis session on a centrifugal cell separator such as a Baxter CS-3000. This product contains desirable mononuclear cells (WBCs), and some undesirable RBCs and platelets. Pump 182 delivers the mononuclear cell (MNC) preparation to spinning membrane separator 148 operating, for example, at 3600 RPM via tubing paths 168 and 142, at a flow rate, for example, of 70 ml/min. The initial volume of MNC may be, for example, 500 ml, and contain, for example $3.8 \times 10^4$ WBC/microliter, $3.3 \times 10^5$ RBC/microliter, and $1.9 \times 10^6$ platelets/microliter.

A fraction of the undesirable platelets and RBCs are passed through membrane 114 into filtrate tubing 166 and into waste bag 180 containing waste 138. This leaves a concentrated suspension, which is higher in WBC concentration than the input concentration 142. The concentrated suspension is drawn from the device gap 140 through concentrate port 144, and tubing 164 by pump 174, and directed back to container 176.

At a point in this process, such as when the volume of concentrated suspension is, for example, 75 ml, as measured by weight scale 184, the system begins operating in a "recirculating mode" which draws concentrated WBC suspension 136 from container 176, adds diluent wash fluid 132, filters the suspension, removes RBCS, platelets, plasma, and wash fluid through filtrate tubing 166 to waste 138. Wash fluid 132 may be introduced by pump 172 and tubing 162 to the input flow in tubing 142. The flow rate of wash fluid, for example, may be approximately 70 ml/min.

The waste flow rate of the removed RBC's platelets, plasma and wash fluid is the net rate of: (pump 182 rate+ pump 172 rate−pump 174 rate) and may be, for example, 70 ml/min with pump 174 operating at 70 ml/min. A control system may be set, for example, to maintain the volume in container 176, at a predetermined volume of 300 ml, by modulating pump 172, 182, or 174, or a combination thereof, in response to the weight scale reading more or less than target volume. After a short time in which, for example, 300 ml of wash fluid have been consumed and the final concentrated WBC suspension 136 is disconnected, an exemplary final product may contain $6.4 \times 10^4$ WBC/ml, $2 \times 10^5$ RBC/ml and $9.7 \times 10^4$ platelets/ml. In this example, the efficiency of platelet removal was high, with Plt/WBC ratio in the original solution being about 50:1 to the Plt/WBC ratio in the final product being about 1.5:1. The RBC/WBC ratio in this typical example was reduced from 8.7 to 3.1, for an RBC/WBC contamination reduction factor of 8.7/3/1=2.8.

By retaining all flow parameters the same (i.e., without further optimization) and only changing from the track-etch polycarbonate membrane having a 3.8 micron circular pore, 7% porosity with approximately 0.1% doublet, to a membrane of this invention (for example, that shown in FIG. 4), the above RBC/WBC contamination reduction factor of 2.8 will be substantially increased due to the shape and deformability selectivity, lack of doublets, and high porosity in the membrane of this invention, and the wash procedure time will be substantially reduced due to the approximate 3.4:1 ratio in the membrane porosities.

Referring again to FIG. 5, exemplary tolerance values are shown on the membrane features. Using the micro fabrication methods previously discussed, filtration membranes satisfying such size and pore positioning tolerances will result in zero doublets, or non-conforming pores. In this way exceptionally pure filtrates can be anticipated. In certain applications, such as RBC transfusion product filtering to remove potentially infected WBCs, product purity will be substantially improved using the membrane structures herein without doublet pores. Additionally, the high porosity of the membranes of this invention allows filtrate flow rates comparable to prior art membranes while using substantially less membrane areas—such as only about 10% to 30%. In systems involving couette flow separation with highly concentrated blood cells in the gap (such as RBC collection, platelet collection, or plasmapheresis) for equivalent shear rate levels, the blood cell exposure times are correspondingly reduced—such as to less than about 20% of prior art systems. The cell exposure time in a shear environment (e.g., the gap in a rotary membrane filter) strongly affects RBC hemolysis and platelet activation. Consequently, these will be substantially reduced by use of the present invention.

While the invention has been described primarily in terms of the separation of blood components, there is no intent to limit the invention to the same. Indeed, the principles of the invention have applicability to the separation of any suspension whose constituent parts have sufficiently distinct size, shape and/or deformation characteristics.

What is claimed is:

1. Apparatus for separating a suspension comprising at least first and second types of particles of different shape, the first type of particle being deformable at a relatively faster rate than the second type of particle, the apparatus including:
   a housing having a generally cylindrical inner surface;
   a rotor having a generally cylindrical outer surface mounted for rotation in said housing, the outer surface of the rotor being spaced from the inner surface of the housing to define a suspension processing gap there between;
   a filter membrane carried by the cylindrical surface of the rotor or the housing, the membrane having a side facing the suspension processing gap and a side facing the cylindrical surface upon which it is carried, the filter membrane having pores with substantially precisely dimensioned shapes and sizes, said pore shapes and sizes being dimensioned to correspond substantially to shape of the first type of particle to allow passage of the first type and to block passage of the second type of particle,
   a suspension inlet in said housing communicating with the suspension processing gap to direct suspension into the processing gap for a selected residence time in contact with the filter membrane, and an outlet communicating with side of the filter membrane facing the cylindrical surface for removing the first type of suspension particle passing through the membrane, the residence time being less than that needed for the second type of particle to deform to a size and shape capable of passing through the membrane.

2. The apparatus of claim 1 in which the filter membrane is carried on the surface of the rotor and defines a curvilinear surface facing the processing gap.

3. The apparatus of claim 1 in which the pores are substantially rectangular in shape and have a width of approximately 1.0 to 3.5 microns and a length of approximately 6 to 14 microns.

4. The apparatus of claim 1 in which the rotor is adapted for rotation at speeds sufficient to create Taylor vortices in said processing gap.

5. The apparatus of claim 1 in which the membrane has a porosity of at least about 10%.

6. Apparatus for separating a suspension comprising at least first and second types of particles of different shape, the first type of particle being deformable at a relatively faster rate than the second type of particle, the apparatus including:
   a housing having a generally cylindrical inner surface;
   a rotor having a generally cylindrical outer surface mounted for rotation in said housing, the outer surface of the rotor being spaced from the inner surface of the housing to define a suspension processing gap there between;
   a filter membrane carried by the cylindrical surface of the rotor or the housing, the membrane having a side facing the suspension processing gap and a side facing the cylindrical surface upon which it is carried, the filter membrane having pores with substantially precisely dimensioned shapes and sizes, said pore shapes and sizes being dimensioned to correspond substantially to shape of the first type of particle to allow passage of the first type and to block passage of the second type of particle,
   a suspension inlet in said housing communicating with the suspension processing gap to direct suspension into the processing gap for contact with the filter membrane at a selected force, and an outlet communicating with the side of the filter membrane facing the cylindrical surface for removing the first type of suspension particle passing through the membrane, the contact force being less than that needed for the second type of particle to deform to a size and shape capable of passing through the membrane.

7. The apparatus of claim 6 in which the filter membrane is carried on the surface of the rotor and defines a curvilinear surface facing the processing gap.

8. The apparatus of claim 6 in which the pores are substantially rectangular in shape and have a width of approximately 1.0 to 3.5 microns and a length of approximately 6 to 14 microns.

9. The apparatus of claim 6 in which the rotor is adapted for rotation at speeds sufficient to create Taylor vortices in said processing gap.

10. The apparatus of claim 6 in which the membrane has a porosity of at least about 10%.

* * * * *